United States Patent
Kim et al.

(10) Patent No.: US 11,023,347 B2
(45) Date of Patent: Jun. 1, 2021

(54) SCREEN CONTROL METHOD AND ELECTRONIC DEVICE SUPPORTING THE SAME

(71) Applicant: SAMSUNG ELECTRONICS CO., LTD., Suwon-si (KR)

(72) Inventors: Dong Hyeon Kim, Suwon-si (KR); Ji Yeon Ma, Seoul (KR); Jin Ha Lee, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 235 days.

(21) Appl. No.: 15/916,904

(22) Filed: Mar. 9, 2018

(65) Prior Publication Data
US 2018/0260295 A1 Sep. 13, 2018

(30) Foreign Application Priority Data
Mar. 9, 2017 (KR) .......................... 10-2017-0030192

(51) Int. Cl.
*G06F 11/30* (2006.01)
*G06F 3/0481* (2013.01)
*G01N 33/00* (2006.01)
*G16Z 99/00* (2019.01)

(52) U.S. Cl.
CPC ..... *G06F 11/3089* (2013.01); *G01N 33/0062* (2013.01); *G06F 3/04815* (2013.01); *G16Z 99/00* (2019.02)

(58) Field of Classification Search
CPC .......... G06F 11/3089; G06F 3/04815; G01N 33/0062; G16Z 99/00; G01D 21/02; G05B 19/0423; G05B 2219/25257
See application file for complete search history.

(56) References Cited

U.S. PATENT DOCUMENTS

| | | | | |
|---|---|---|---|---|
| 5,122,801 A | * | 6/1992 | Hughes | G01S 7/021 342/13 |
| 8,196,085 B1 | * | 6/2012 | Milton | G06F 30/327 716/133 |
| 8,577,505 B2 | * | 11/2013 | Foslien | B60H 1/00985 700/275 |
| 8,941,656 B2 | * | 1/2015 | Bak | G06T 11/206 345/428 |
| 9,070,227 B2 | * | 6/2015 | Drucker | G06T 11/206 |
| 9,103,805 B2 | | 8/2015 | Gettings et al. | |

(Continued)

OTHER PUBLICATIONS

"Underwater exploration like a game . . . Com2us 'iQuarium'", BLOTER, Sep. 3, 2012, 6 pages total, http://www.bloter.net/newsView/blt201209030004.

(Continued)

*Primary Examiner* — Yongjia Pan
(74) *Attorney, Agent, or Firm* — Sughrue Mion, PLLC

(57) ABSTRACT

An electronic device includes a sensor that senses an external environment, a display that outputs a first screen including one or more movable particles, a memory, and a processor electrically connected with the sensor, the display, and the memory. The memory stores instructions that, when executed, cause the processor to obtain first information about the external environment through the sensor and to change a display state of a first particle of the one or more movable particles, based on a result obtained by analyzing the first information.

14 Claims, 10 Drawing Sheets

(56) References Cited

U.S. PATENT DOCUMENTS

| | | | |
|---|---|---|---|
| 9,195,364 B2* | 11/2015 | Zhang | G06T 13/20 |
| 2008/0263468 A1* | 10/2008 | Cappione | G06F 3/04817 |
| | | | 715/771 |
| 2011/0083094 A1* | 4/2011 | Laycock | G06F 9/451 |
| | | | 715/772 |
| 2013/0007604 A1* | 1/2013 | John | G06F 3/0488 |
| | | | 715/255 |
| 2013/0018513 A1* | 1/2013 | Metselaar | G05D 23/1902 |
| | | | 700/278 |
| 2013/0111386 A1* | 5/2013 | Rhodes | G06F 9/5077 |
| | | | 715/771 |
| 2013/0283208 A1* | 10/2013 | Bychkov | G06F 3/017 |
| | | | 715/810 |
| 2014/0210639 A1* | 7/2014 | Skourlis | G01D 4/002 |
| | | | 340/870.16 |
| 2014/0278260 A1 | 9/2014 | Gettings et al. | |
| 2014/0279574 A1 | 9/2014 | Gettings et al. | |
| 2014/0281479 A1* | 9/2014 | Gettings | G01N 33/0062 |
| | | | 713/150 |
| 2017/0041407 A1* | 2/2017 | Wilbur | H04L 67/18 |
| 2017/0108885 A1* | 4/2017 | Meganathan | G05B 13/041 |

OTHER PUBLICATIONS

Communication dated Mar. 30, 2021 by the Korean Intellectual Property Office in counterpart Korean Patent Application No. 10-2017-0030192.

* cited by examiner

SCREEN CONTROL METHOD AND ELECTRONIC DEVICE SUPPORTING THE SAME

CROSS-REFERENCE TO RELATED APPLICATION(S)

This application is based on and claims priority under 35 U.S.C. § 119 to Korean Patent Application No. 10-2017-0030192, filed on Mar. 9, 2017, in the Korean Intellectual Property Office, the disclosure of which is incorporated by reference herein in its entirety.

BACKGROUND

1. Field

The disclosure relates to a screen control method and an electronic device supporting the same.

2. Description of Related Art

With the rapid development into a ubiquitous society, electronic devices including a display are capable of supporting the use of various visual resources. In addition, recent electronic devices are aimed at constructing communication infrastructure between electronic devices and people and are developing into newer aspects of platforms. For example, an electronic device disposed in a public space, such as an exhibition space or a working space, or in a private space, such as a living room, may provide what is called a media art image that implements various images by aesthetically combining dynamic particles displayed on a screen.

The above information is presented as background information only to assist with an understanding of the disclosure. No determination has been made, and no assertion is made, as to whether any of the above might be applicable as prior art with regard to the disclosure.

SUMMARY

However, since a conventional electronic device for providing a media art image is aimed at simply creating an aesthetic effect, practicality of the electronic device may be specifically limited or minimal.

Aspects of the disclosure are to address at least the above-mentioned problems and/or disadvantages and to provide at least the advantages described below. Accordingly, an aspect of the disclosure is to provide a screen control method for visually providing information about an external environment, for example, temperature, humidity, carbon dioxide concentration, organic chemical concentration, or fine dust concentration by using dynamic particles constituting a media art image, and to provide an electronic device supporting the screen control method.

In accordance with an aspect of the disclosure, an electronic device includes a sensor that senses an external environment, a display that outputs a first screen including one or more movable particles, a memory, and a processor electrically connected with the sensor, the display, and the memory. The memory stores instructions that, when executed, cause the processor to obtain first information about the external environment through the sensor and to change a display state of a first particle of the one or more movable particles, based on a result obtained by analyzing the first information.

In accordance with another aspect of the disclosure, a screen control method of an electronic device includes outputting a first screen including one or more movable particles on a display, obtaining first information about an external environment through a sensor, and changing a display state of a first particle of the one or more movable particles, based on a result obtained by analyzing the first information.

In accordance with yet another aspect of the disclosure, there is an electronic device comprising: a sensor configured to sense an external environment that is external to the electronic device; a display configured to display a first screen, the displayed first screen comprising one or more movable particles that are displayed; a memory; and a processor electrically connected with the sensor, the display, and the memory, wherein the memory stores instructions that, when executed, cause the processor to: obtain first information about the external environment from the sensor; and change a display state of a first particle of the one or more movable particles, based on a result obtained by analyzing the first information.

In accordance with another aspect of the disclosure, there is a screen control method of an electronic device, the method comprising: outputting a first screen including one or more movable particles on a display; obtaining first information about an external environment through a sensor; and changing a display state of a first particle of the one or more movable particles, based on a result obtained by analyzing first information.

According to embodiments disclosed herein, by visually providing information about an external environment through a media art image, it is possible to achieve an aesthetic effect with practicality.

In addition, the disclosure may provide various effects that are directly or indirectly recognized.

Other aspects and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

Figure 1:
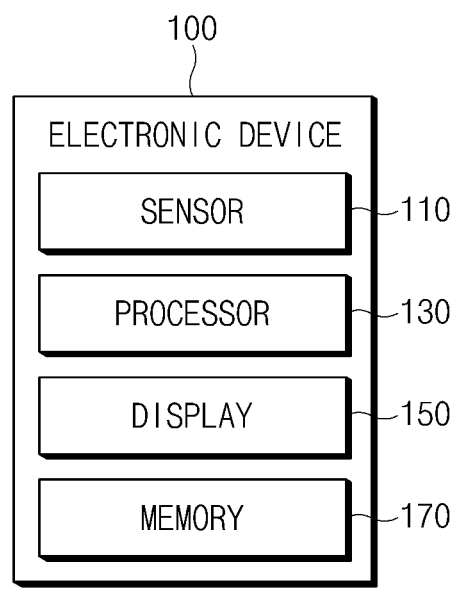
FIG. 1 is a block diagram of an electronic device related to screen control according to an embodiment.

Hereinafter, various embodiments of the disclosure will be described with reference to accompanying drawings. Accordingly, those of ordinary skill in the art will recognize that modification, equivalent, and/or alternative on the various embodiments described herein can be variously made without departing from the scope and spirit of the disclosure. With regard to description of drawings, similar elements may be marked by similar reference numerals.

FIG. 1 is a block diagram of an electronic device related to screen control according to an embodiment.

An electronic device 100 may display various pieces of contents through a display 150. For example, the electronic device 100 may output, on the display 150, an execution screen of an application stored in a memory 170. The execution screen of the application may include a screen, such as a media art image, to which an aesthetic element is added. The media art image may include various graphical elements, such as particles or images, which are generated by a program. Furthermore, a real-time rendered screen may be displayed on the display 150 by converting the graphical elements into a new form of graphics by mathematical calculation.

Furthermore, the electronic device 100 may visually represent information about an external environment through the display 150. In an embodiment, the external environment is external to the display 150. For example, the electronic device 100 may measure temperature, humidity, carbon dioxide concentration, organic chemical concentration, or fine dust concentration through a sensor 110, may generate movable (dynamic) particles based on the measured data, and may output a screen (e.g., a media art image) including the generated particles on the display 150.

Referring to FIG. 1, the electronic device 100 for performing the above-described function may include the sensor 110, a processor 130, the display 150, and the memory 170. However, a configuration of the electronic device 100 is not limited thereto. According to various embodiments, the electronic device 100 may not include at least one of the aforementioned elements and may further include at least one other element. For example, the electronic device 100 may further include a communication circuit for communicating with an external electronic device, a camera for photographing a subject, or an interface (e.g., an input device) for receiving a user input.

The sensor 110 may measure a physical quantity or sense an operating state of the electronic device 100 and may convert the measured or sensed information into an electrical signal. The sensor 110 may measure information about an external environment of the electronic device 100. According to an embodiment, the sensor 110 may measure temperature, humidity, carbon dioxide concentration, organic chemical concentration, or fine dust concentration in a space where the electronic device 100 is located. The sensor 110 may include, for example, a temperature sensor, a humidity sensor, a gas sensor, a dust sensor, or a pollution level measurement sensor.

The processor 130 may perform operations or data processing related to control and/or communication of at least one other element of the electronic device 100. The processor 130 may drive, for example, an operating system or an application program (application) to control a plurality of hardware or software elements connected to the processor 130 and to perform various types of data processing or operations. The processor 130 may load a command or data received from at least one of other elements (e.g., a non-volatile memory) into a volatile memory to process the command or data and may store various data into a non-volatile memory. For example, the processor 130 may load a command or data related to screen control into the volatile memory to process the command or data according to a specified program routine. The processor 130 may include one or more of a central processing unit (CPU), an application processor (AP), and a communication processor (CP).

According to an embodiment, the processor 130 may analyze information about an external environment of the electronic device 100 that is obtained through the sensor 110. For example, the processor 130 may analyze temperature, humidity, carbon dioxide concentration, organic chemical concentration, or fine dust concentration in a space where the electronic device 100 is located, and may compute an overall environmental index for the space.

According to an embodiment, the processor 130 may map information (e.g., temperature, humidity, carbon dioxide concentration, organic chemical concentration, and fine dust concentration) used for assessment of the external environment onto particles having different shapes. For example, the processor 130 may map temperature information, humidity information, carbon dioxide concentration information, organic chemical concentration information, and fine dust concentration information onto a circular particle, a triangular particle, a rectangular particle, a pentagonal particle, and a hexagonal particle, respectively. However, the shapes of the particles onto which the information is mapped are not limited thereto. Furthermore, even though the particles onto which the information is mapped have the same shape, the processor 130 may distinguish the information by making other graphical elements of the particles different from one another. For example, the processor 130 may make the colors, sizes, border thicknesses, or border colors of the particles different from one another to distinguish between the particles mapped onto the information.

According to an embodiment, the processor 130 may differently set display states of the particles mapped onto the information, based on a result obtained by analyzing the information used for assessment of the external environment. For example, with an increase in temperature, humidity, carbon dioxide concentration, organic chemical concentration, and fine dust concentration, the processor 130 may increase the number of particles corresponding thereto. In another example, with an increase in temperature, humidity, carbon dioxide concentration, organic chemical concentration, and fine dust concentration, the processor 130 may increase the moving speed of particles corresponding thereto. In another example, with an increase in temperature, humidity, carbon dioxide concentration, organic chemical concentration, and fine dust concentration, the processor 130 may increase the size or the border thickness of particles corresponding thereto, or may make the color or the border color thereof dark.

According to an embodiment, the processor 130 may differently set display time of the particles (e.g., time periods during which the particles are displayed on the display 150). For example, the processor 130 may differently set display time according to display states (e.g., shape, color, and the like) of the particles. Furthermore, the processor 130 may differently set the number of particles mapped onto the information used for assessment of the external environment. For example, the processor 130 may set the number of first particles mapped onto temperature to a first range, may set the number of second particles mapped onto humidity to a second range, may set the number of third particles mapped onto carbon dioxide concentration to a third range, may set the number of fourth particles mapped onto organic chemical concentration to a fourth range, and may set the number of fifth particles mapped onto fine dust concentration to a fifth range. Accordingly, if particles having any one display state move for a specified period of time and then disappear, the processor 130 may generate other particles having the display state within a specified range.

According to an embodiment, in the case where the electronic device 100 includes a camera, the processor 130 may obtain an image of a subject (e.g., a user) through the camera. Furthermore, the processor 130 may analyze the image. For example, the processor 130 may detect an object included in the image. The processor 130 may extract feature points from the image and may detect a shape (e.g., an omega shape) constituted by adjacent feature points, among the feature points, as an object (e.g., a face). The feature points may be, for example, points that represent a feature of the image to detect, track, or recognize an object in the image, and may include points that are easily distinguishable despite a change in the shape, size, or position of each object in the image. Furthermore, the feature points may include points that are easily distinguishable in the image even though the camera angle or lighting changes. The feature points may be set as, for example, corner points or boundary points of each object.

According to an embodiment, the processor 130 may distinguish between objects included in the image. For example, the processor 130 may determine whether the corresponding objects are a person, an animal, or an object. In addition, the processor 130 may determine a body part (e.g., a face, a hand, or the like) of a person, the type of animal, or the type of object to distinguish the objects.

According to an embodiment, the processor 130 may determine a user's motion (or a motion of a part of the user's body) based on a result obtained by analyzing an image. The processor 130 may track a feature point corresponding to the user (or the part of the user's body), among feature points included in the image, to determine a moving direction and a moving speed of the user (or the part of the user's body).

According to an embodiment, the processor 130 may set a moving direction and a moving speed of particles used for assessment of the external environment, based on the moving direction and the moving speed of the user (or the part of the user's body). For example, the processor 130 may change the position of particles disposed on a screen to correspond to a change in the position of the user (or the part of the user's body). For example, when the user's hand moves from the left to the right of the screen in the state in which the user's hand is in proximity to the screen, the processor 130 may move particles disposed in a screen area close to the user's hand from the left to the right of the screen according to the moving direction and speed of the user's hand.

According to an embodiment, in the case where the electronic device 100 includes an interface (e.g., an input device) for receiving a user input or the sensor 110 includes a proximity sensor, the processor 130 may obtain a user's interaction through the input device or the proximity sensor. The input device may include, for example, a microphone for receiving the user's speech, a touch sensor for the user's touch input, or a physical button for the user's button input.

According to an embodiment, in the case where the user's interaction obtained through the input device or the proximity sensor satisfies a specified condition, the processor 130 may output a screen including detailed information about an external environment on the display 150. For example, in the case where the user's speech received through the microphone includes a command to output detailed information about temperature, humidity, carbon dioxide concentration, organic chemical concentration, or fine dust concentration, the processor 130 may output a screen representing detailed information of the corresponding information on the display 150. In another example, when detecting the user (or a part of the user's body) within a specified distance through the proximity sensor, the processor 130 may output a screen including detailed information of an external environment on the display 150.

According to an embodiment, in the case where the electronic device 100 includes a communication circuit for communication with an external electronic device, the processor 130 may obtain, from the external electronic device, environmental information about a space where the electronic device 100 is located or environmental information about a space other than the space. For example, the processor 130 may obtain information about temperature, humidity, carbon dioxide concentration, organic chemical concentration, or fine dust concentration in an area where the electronic device 100 is located or in another area, from a server in a weather center through the communication circuit.

According to an embodiment, the processor 130 may configure a screen such that information obtained through the sensor 110 is distinguished from information obtained from the external electronic device, and may output the screen on the display 150. For example, the processor 130 may generate a boundary line that divides a central area of the screen from a peripheral area thereof and may dispose particles corresponding to the information obtained through the sensor 110 in the central area inside the boundary line and particles corresponding to the information obtained from the external electronic device in the peripheral area outside the boundary line. Furthermore, the processor 130 may adjust a moving position of a first particle disposed in the central area to prevent the first particle from deviating from the central area (intruding into the peripheral area) even though the first particle moves. Likewise, the processor 130 may adjust a moving position of a second particle disposed in the peripheral area to prevent the second particle from deviating from the peripheral area (intruding into the central area) even though the second particle moves.

The display 150 may display various types of contents for a user. For example, the display 150 may display a media art image including dynamic particles. According to an embodiment, the display 150 may include a touch screen and may receive, for example, a touch input, a gesture input, a proximity input, or a hovering input using an electronic pen or a part of the user's body.

The memory 170 may include a volatile memory and/or a non-volatile memory. For example, the memory 170 may store one or more instructions or data related to at least one other element of the electronic device 100. According to an embodiment, the memory 170 may store software and/or a program. The program may include an application. The application may be a set of programs (or instructions) for performing at least one specified function and may include, for example, an image reproduction application. The image reproduction application may include instructions to output a media art image stored in the memory 170 on the display 150. The memory 170 may include an internal memory or an external memory.

As described above, according to various embodiments, an electronic device (e.g., the electronic device 100) may include a sensor (e.g., the sensor 110) that senses an external environment, a display (e.g., the display 150) that outputs a first screen including one or more movable particles, a memory (e.g., the memory 170), and a processor (e.g., the processor 130) electrically connected with the sensor, the display, and the memory. The memory may store instructions that, when executed, cause the processor to obtain first information about the external environment through the sensor and to change a display state of a first particle of the one or more movable particles, based on a result obtained by analyzing the first information.

According to various embodiments, the memory may store instructions that, when executed, cause the processor to differently set at least one of a shape, a size, a color, and display time of the first particle according to at least one attribute of the first information. The attribute of the first information, for example, may be the types of the information about an external environment that a processor (e.g., the processor 110) detects through sensor (e.g., the sensor 110). The external environment may be the external to the electronic device.

According to various embodiments, the memory may store instructions that, when executed, cause the processor to differently set at least one of a position of the first particle, the number of first particles, and a moving speed of the first particle, based on at least one value measured for at least one attribute of the first information.

According to various embodiments, the electronic device may further include a camera, and the memory may store instructions that, when executed, cause the processor to obtain an image of a user through the camera, to determine a motion of the user, based on a result obtained by analyzing the image, and to set a moving direction and a moving speed of the first particle, based on a direction and a speed of the motion.

According to various embodiments, the electronic device may further include an interface for a user's interaction, and the memory may store instructions that, when executed, cause the processor to obtain the user's interaction through the interface and to output a second screen including detailed information about the first information through the display when the user's interaction satisfies a specified condition.

According to various embodiments, the interface may include at least one of a proximity sensor that senses proximity of the user to the electronic device, a microphone that receives speech of the user, a touch sensor that obtains a touch input of the user, and a physical button that generates a signal in response to a button input of the user.

According to various embodiments, the electronic device may further include a communication circuit for communication with an external electronic device, and the memory may store instructions that, when executed, cause the processor to obtain second information about another external environment from the external electronic device through the communication circuit and to change a display state of a second particle of the one or more movable particles, based on a result obtained by analyzing the second information.

According to various embodiments, the memory may store instructions that, when executed, cause the processor to move the first particle in only a first area of the first screen and to move the second particle in only a second area that is located outside the first area to surround the first area.

According to various embodiments, the memory may store instructions that, when executed, cause the processor to differently set at least one from among a shape, a size, a color, and display time of the second particle according to at least one attribute of the second information. The attribute of the second information, for example, may be the types of the information about an external environment that an electronic apparatus (e.g., the electronic apparatus 100) detects through the external electronic device. The other external environment may be the external to the electronic device.

According to various embodiments, the memory may store instructions that, when executed, cause the processor to differently set at least one from among a position of the second particle, the number of second particles, and a moving speed of the second particle, based on at least one value measured for at least one attribute of the second information.

Figure 2:
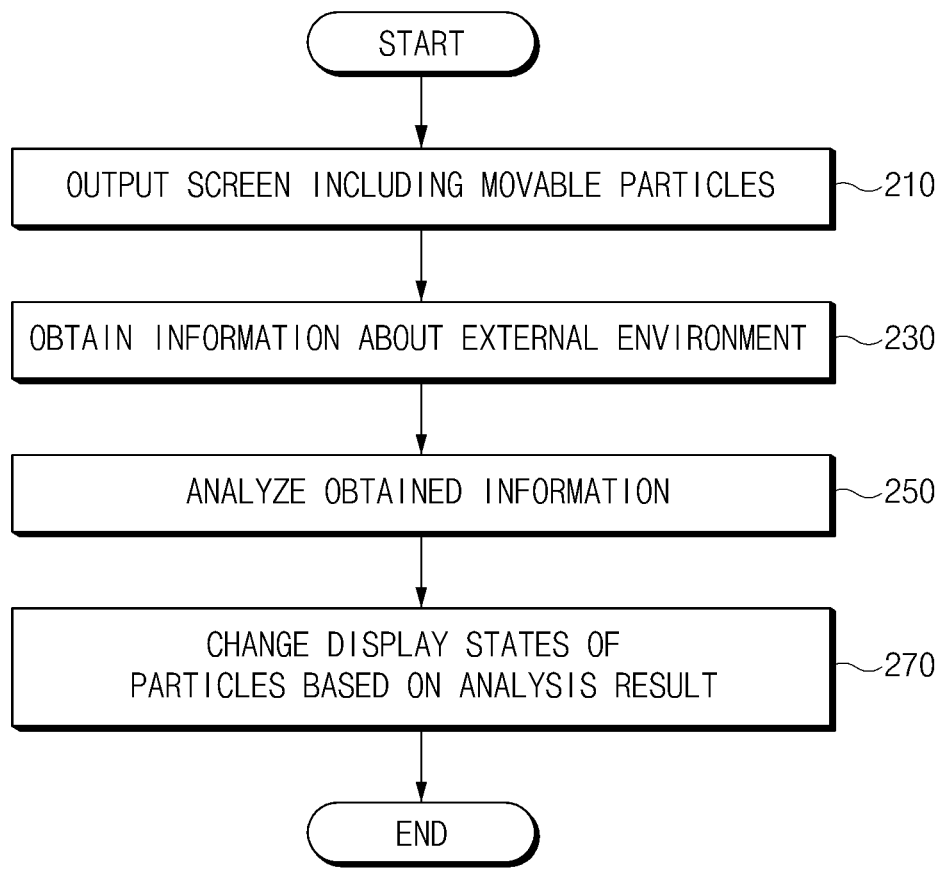
FIG. 2 is a view illustrating an operating method of an electronic device related to screen control for providing information according to an embodiment.

FIG. 2 is a view illustrating an operating method of an electronic device related to screen control for providing information according to an embodiment.

Referring to FIG. 2, in operation 210, an electronic device (e.g., the electronic device 100) may output a screen including movable particles on a display (e.g., the display 150). For example, the electronic device (e.g., the processor 130) may output a media art image including movable particles on the display.

In operation 230, the electronic device (e.g., the processor 130) may obtain, through a sensor (e.g., the sensor 101), information about an external environment, for example, temperature information, humidity information, carbon dioxide concentration information, organic chemical concentration information, or fine dust concentration information. Furthermore, in operation 250, the electronic device (e.g., the processor 130) may analyze the information obtained through the sensor. For example, the electronic device (e.g., the processor 130) may measure temperature, humidity, carbon dioxide concentration, organic chemical concentration, or fine dust concentration through the sensor and may compute an environmental index for the external environment, based on the measured data. According to an embodiment, the electronic device may not perform operation 250 in the case where the information obtained through the sensor is processed data (e.g., data processed as information that a user is able to recognize) for the external environment.

In operation 270, the electronic device (e.g., the processor 130) may change display states of the particles, based on the analysis result (or the obtained information). For example, with an increase in temperature, humidity, carbon dioxide concentration, organic chemical concentration, and fine dust concentration, the electronic device (e.g., the processor 130) may increase the number of particles corresponding thereto. In another example, with an increase in temperature, humidity, carbon dioxide concentration, organic chemical concentration, and fine dust concentration, the electronic device (e.g., the processor 130) may increase the moving speed of particles corresponding thereto. In another example, with an increase in temperature, humidity, carbon dioxide concentration, organic chemical concentration, and fine dust concentration, the electronic device (e.g., the processor 130) may increase the size or the border thickness of particles corresponding thereto, or may make the color or the border color thereof dark.

Also, the reverse is possible. For example, with a decrease in temperature, humidity, carbon dioxide concentration, organic chemical concentration, and fine dust concentration, the electronic device (e.g., the processor 130) may decrease the number of particles corresponding thereto. In another example, with a decrease in temperature, humidity, carbon dioxide concentration, organic chemical concentration, and fine dust concentration, the electronic device (e.g., the processor 130) may decrease the moving speed of particles corresponding thereto. In another example, with a decrease in temperature, humidity, carbon dioxide concentration, organic chemical concentration, and fine dust concentration, the electronic device (e.g., the processor 130) may decrease the size or the border thickness of particles corresponding thereto, or may make the color or the border color thereof light.

Figure 3:
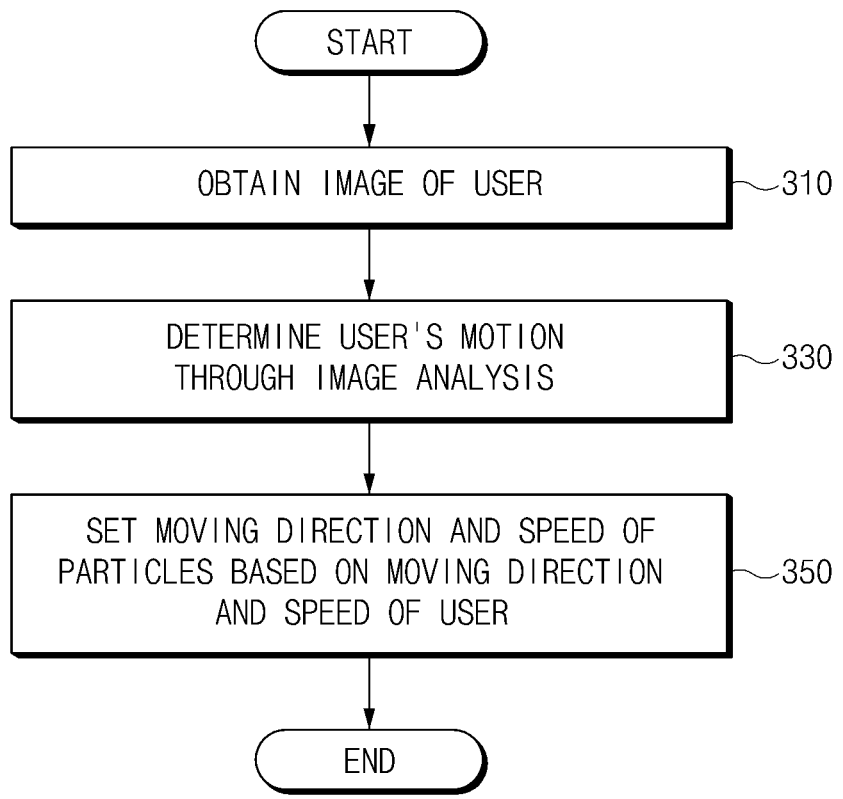
FIG. 3 is a view illustrating an operating method of an electronic device related to screen control based on a user's motion according to an embodiment.

FIG. 3 is a view illustrating an operating method of an electronic device related to screen control based on a user's motion according to an embodiment.

Referring to FIG. 3, in operation 310, an electronic device (e.g., the electronic device 100) may obtain an image of a user through a camera. The electronic device (e.g., the processor 130) may control the camera to take an image of the user at a specified time interval for a specified period of time. Furthermore, the electronic device (e.g., the processor 130) may store the image of the user in a memory (e.g., the memory 170).

In operation 330, the electronic device (e.g., the processor 130) may analyze the image and may determine the user's motion based on the analysis result. For example, the electronic device (e.g., the processor 130) may determine a moving direction and a moving speed of the user by tracking a feature point corresponding to the user, among feature points included in the image.

In operation 350, the electronic device (e.g., the processor 130) may change a screen including movable particles, which is output on a display (e.g., the display 150), based on the moving direction and speed of the user. For example, the electronic device (e.g., the processor 130) may set a moving direction and a moving speed of the particles to correspond to the moving direction and the moving speed of the user. For example, when the user moves from the left to the right of the screen in the state in which the user is in proximity to the screen, the electronic device (e.g., the processor 130) may move particles disposed in a screen area close to the user from the left to the right of the screen at a speed similar to the moving speed of the user in a direction similar to the moving direction of the user. According to an embodiment, the electronic device (e.g., the processor 130) may determine a motion of a part (e.g., a hand) of the user's body and may set a moving direction and a moving speed of the particles, based on the motion of the part of the user's body.

Figure 4:
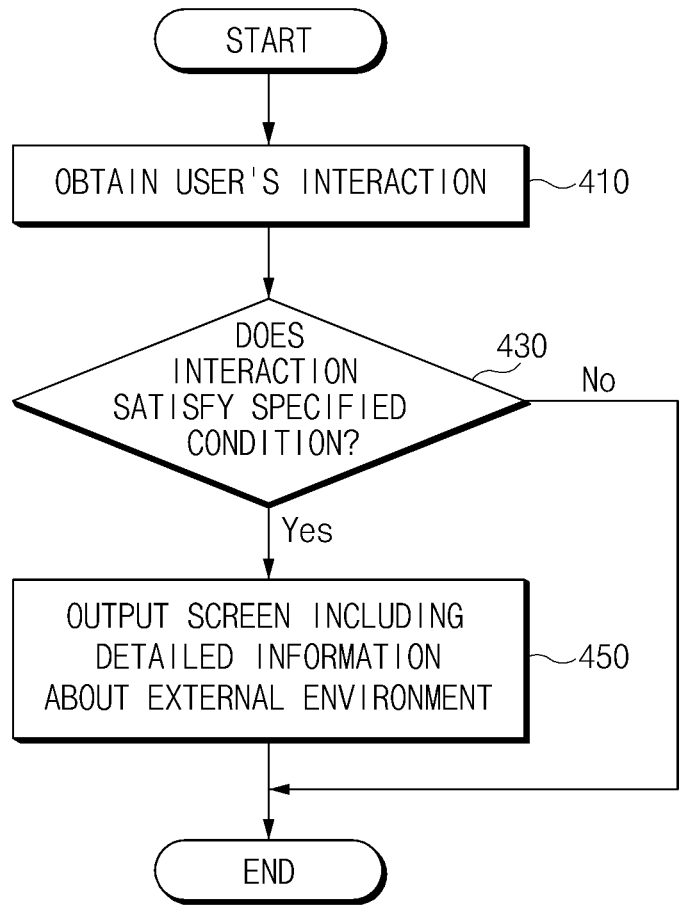
FIG. 4 is a view illustrating an operating method of an electronic device related to screen control through an interaction with a user according to an embodiment.

FIG. 4 is a view illustrating an operating method of an electronic device related to screen control through an interaction with a user according to an embodiment.

Referring to FIG. 4, in operation 410, an electronic device (e.g., the electronic device 100) may obtain a user's interaction through an input device (e.g., a microphone, a touch sensor, or a physical button) or a sensor (e.g., the sensor 110). For example, the electronic device (e.g., the processor 130) may obtain the user's speech through the microphone, may obtain the user's touch input through the touch sensor, or may receive a signal generated from the physical button. In another example, the electronic device (e.g., the processor 130) may determine (detect) the user's proximity to the electronic device through the sensor (e.g., a proximity sensor).

In operation 430, the electronic device (e.g., the processor 130) may determine whether the user's interaction satisfies a specified condition. For example, the electronic device (e.g., the processor 130) may determine whether the user's interaction obtained through the input device or the sensor corresponds to a user input associated with outputting detailed information about an external environment. For example, the electronic device (e.g., the processor 130) may perform speech recognition on speech data received through the microphone and may determine whether a command to output the detailed information about the external environment is included in the speech recognition result. Alternatively, the electronic device (e.g., the processor 130) may analyze a touch input obtained through the touch sensor and may determine, based on the analysis result, whether the touch input corresponds to a user input for selecting a display object configured to output the detailed information about the external environment. In another case, the electronic device (e.g., the processor 130) may determine whether the physical button corresponds to a physical button configured to output the detailed information about the external environment. In another example, the electronic device (e.g., the processor 130) may determine, through the sensor (e.g., a proximity sensor), whether the user is within a specified distance.

In the case where the user's interaction satisfies the specified condition, the electronic device (e.g., the processor 130) may, in operation 450, output a screen including the detailed information about the external environment on a display (e.g., the display 150). For example, the electronic device (e.g., the processor 130) may output, on the display, a screen representing detailed information on at least one from among temperature, humidity, carbon dioxide concentration, organic chemical concentration, and fine dust concentration. The detailed information about the external environment may include, for example, an overall environmental index for a space where the electronic device is located. Furthermore, the detailed information about the external environment may be displayed in a text or graph format on the display.

As described above, according to various embodiments, a screen control method of an electronic device (e.g., the electronic device 100) may include outputting a first screen including one or more movable particles on a display, obtaining first information about an external environment through a sensor, and changing a display state of a first particle of the one or more movable particles, based on a result obtained by analyzing the first information.

According to various embodiments, the screen control method may further include differently setting at least one from among a shape, a size, a color, and display time of the first particle according to at least one attribute of the first information.

According to various embodiments, the screen control method may further include differently setting at least one from among a position of the first particle, the number of first particles, and a moving speed of the first particle, based on at least one value measured for at least one attribute of the first information.

According to various embodiments, the screen control method may further include obtaining an image of a user through a camera, determining a motion of the user, based on a result obtained by analyzing the image, and setting a moving direction and a moving speed of the first particle, based on a direction and a speed of the motion.

According to various embodiments, the screen control method may further include obtaining a user's interaction through an interface and outputting a second screen including detailed information about the first information through the display when the user's interaction satisfies a specified condition.

According to various embodiments, the obtaining of the user's interaction may include sensing proximity of the user to the electronic device through a proximity sensor, obtaining speech of the user through a microphone, obtaining a touch input of the user through a touch sensor, or receiving, from a physical button, a signal generated in response to a button input of the user.

According to various embodiments, the screen control method may further include obtaining second information about another external environment from an external electronic device through a communication circuit and changing a display state of a second particle of the one or more movable particles, based on a result obtained by analyzing the second information.

According to various embodiments, the screen control method may further include moving the first particle in only a first area of the first screen and moving the second particle in only a second area that is located outside the first area to surround the first area.

According to various embodiments, the screen control method may further include differently setting at least one from among a shape, a size, a color, and display time of the second particle according to at least one attribute of the second information.

According to various embodiments, the screen control method may further include differently setting at least one from among a position of the second particle, the number of second particles, and a moving speed of the second particle, based on at least one value measured for at least one attribute of the second information.

Figure 5:
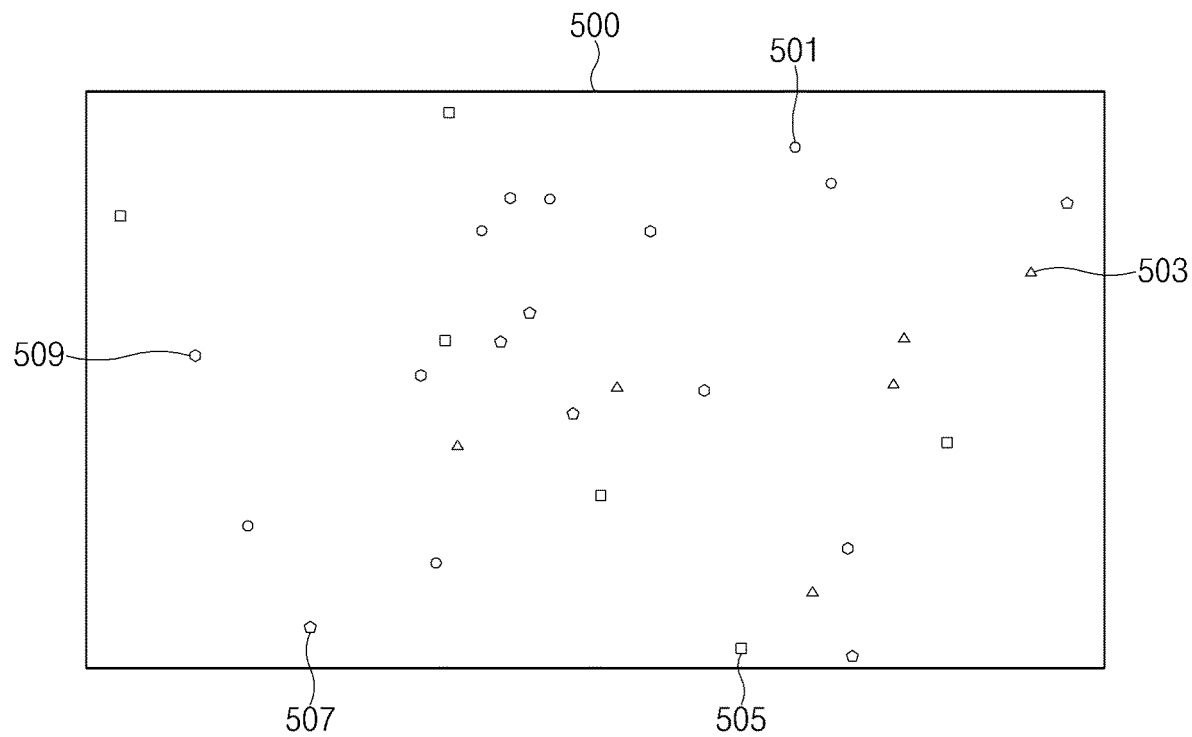
FIG. 5 is a view for explaining a screen including dynamic particles according to an embodiment.

FIG. 5 is a view for explaining a screen including dynamic particles according to an embodiment.

Referring to FIG. 5, an electronic device (e.g., the electronic device 100) may generate information about an external environment (e.g., temperature information, humidity information, carbon dioxide concentration information, organic chemical concentration information, or fine dust concentration information) by using sensing data obtained through a sensor (e.g., the sensor 110), may generate movable (dynamic) particles based on the generated information, and may output a media art image 500 (e.g., a media art image) including the generated particles on a display (e.g., the display 150). Alternatively, in the case where the media art image 500 is output on the display, the electronic device may map the information (e.g., temperature information, humidity information, carbon dioxide concentration information, organic chemical concentration information, or fine dust concentration information) used for assessment of the external environment onto the particles constituting the media art image 500. For example, the electronic device may map temperature information, humidity information, carbon dioxide concentration information, organic chemical concentration information, and fine dust concentration information onto first particles 501, second particles 503, third particles 505, fourth particles 507, and fifth particles 509, respectively.

According to an embodiment, the electronic device (e.g., the processor 130) may output the media art image 500 (or the screen including the particles) on the display by executing an image reproduction application stored in a memory (e.g., the memory 170). In this case, the electronic device may represent approximate information about the external environment by mapping the information used for assessment of the external environment onto the particles constituting the media art image 500 and setting display states of the particles according to data values of the information. According to an embodiment, the electronic device (e.g., the processor 130) may also output the media art image 500 (or the screen including the particles) on the display by executing an external-environment measurement application. In this case, the electronic device may generate particles corresponding to data values of the information used for assessment of the external environment, may configure the media art image 500 with the generated particles, and may output the media art image 500 on the display.

The particles constituting the media art image 500 may have a graphical element (e.g., shape, color, size, border thickness, border color, or the like) differently set according to the type of corresponding environmental information. For example, the first particles 501 corresponding to temperature information, the second particles 503 corresponding to humidity information, the third particles 505 corresponding to carbon dioxide concentration information, the fourth particles 507 corresponding to organic chemical concentration information, and the fifth particles 509 corresponding to fine dust concentration information may have a circular shape, a triangular shape, a rectangular shape, a pentagonal shape, and a hexagonal shape, respectively.

According to an embodiment, the electronic device (e.g., the processor 130) may set display states of the particles corresponding to the environmental information, based on data values of the environmental information. For example, with an increase in temperature, humidity, carbon dioxide concentration, organic chemical concentration, and fine dust concentration, the electronic device may increase the number, moving speed, size, or border thickness of the first to fifth particles 501, 503, 505, 507, and 509 corresponding thereto, or may make the color or the border color thereof dark. In contrast, with a decrease in temperature, humidity, carbon dioxide concentration, organic chemical concentration, and fine dust concentration, the electronic device may decrease the number, moving speed, size, or border thickness of the first to fifth particles 501, 503, 505, 507, and 509 corresponding thereto, or may make the color or the border color thereof light.

According to an embodiment, the electronic device (e.g., the processor 130) may differently set display time of the particles corresponding to the environmental information (e.g., a time range from display start time to display end time). For example, the electronic device may set first display time, second display time, third display time, fourth display time, and fifth display time for the first particles 501 corresponding to temperature information, the second particles 503 corresponding to humidity information, the third particles 505 corresponding to carbon dioxide concentration information, the fourth particles 507 corresponding to organic chemical concentration information, and the fifth particles 509 corresponding to fine dust concentration information, respectively. The first display time, the second display time, the third display time, the fourth display time, and the fifth display time may be the same as one another, or at least one thereof may be different from the others.

According to an embodiment, the electronic device (e.g., the processor 130) may restrict, to a specified range, the number of particles on the media art image 500 that correspond to the environmental information. For example, the electronic device may restrict the number of first particles 501 on the media art image 500 that correspond to temperature information, the number of second particles 503 on the media art image 500 that correspond to humidity information, the number of third particles 505 on the media art image 500 that correspond to carbon dioxide concentration information, the number of fourth particles 507 on the media art image 500 that correspond to organic chemical concentration information, and the number of fifth particles 509 on the media art image 500 that correspond to fine dust concentration information to a first range, a second range, a third range, a fourth range, and a fifth range, respectively. The first range, the second range, the third range, the fourth range, and the fifth range may be the same as one another, or at least one thereof may be different from the others.

Figure 6:
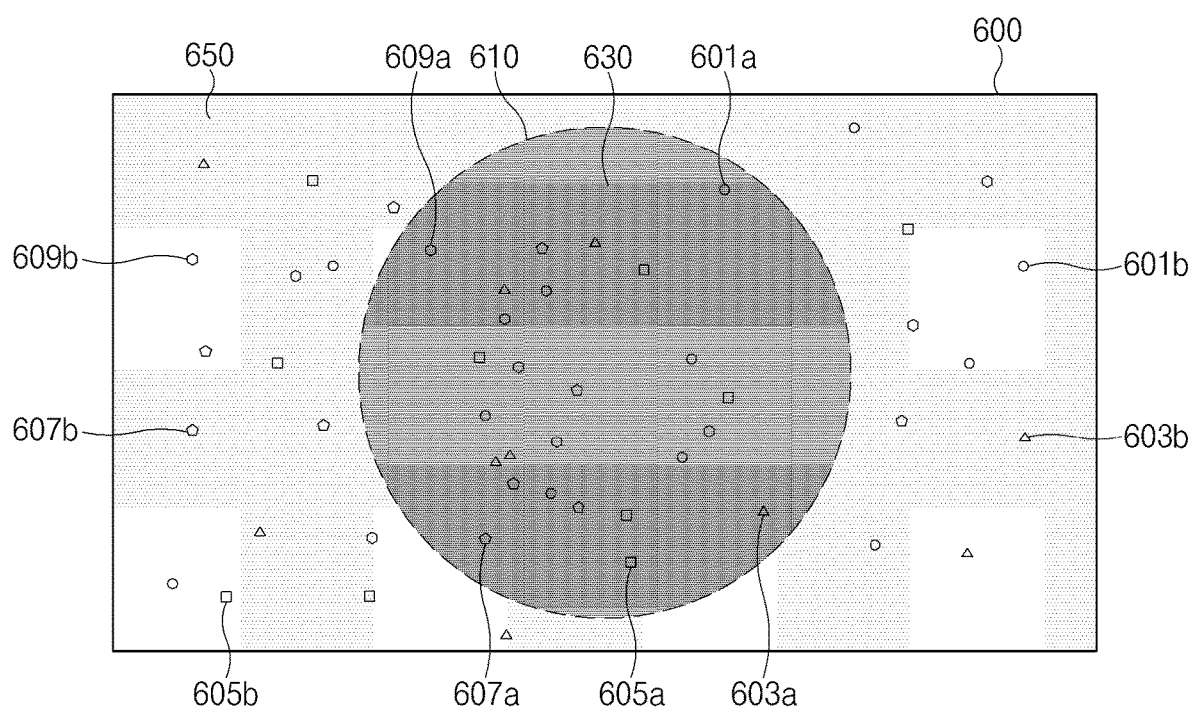
FIG. 6 is a view for explaining the provision of information using dynamic particles according to an embodiment.

FIG. 6 is a view for explaining the provision of information using dynamic particles according to an embodiment.

An electronic device (e.g., the electronic device 100) may obtain, based on a sensor (e.g., the sensor 110), environmental information (e.g., temperature information, humidity information, carbon dioxide concentration information, organic chemical concentration information, or fine dust concentration information) about a space where the electronic device is located. Furthermore, the electronic device may be connected with an external electronic device (e.g., a server in a weather center) through a communication circuit and may obtain, from the external electronic device, environmental information about the space where the electronic device is located or environmental information about a space other than the space. In this case, the electronic device (e.g., the processor 130) may output, on a display (e.g., the display 150), a screen 600 (e.g., a media art image) that includes movable particles and is configured based on the environmental information obtained from the external electronic device, as well as the environmental information obtained through the sensor.

Referring to FIG. 6, the electronic device (e.g., the processor 130) may configure the screen 600 such that particles corresponding to the environmental information obtained through the sensor are distinguished from particles corresponding to the environmental information obtained from the external electronic device. For example, the electronic device may generate a boundary line 610 that divides a central area 630 of the screen 600 from a peripheral area 650 thereof, and may dispose the particles corresponding to the environmental information obtained through the sensor in the central area 630 inside the boundary line 610 and the particles corresponding to the environmental information obtained from the external electronic device in the peripheral area 650 outside the boundary line 610. Alternatively, the electronic device may dispose, in the central area 630, the particles corresponding to the environmental information about the space where the electronic device is located, and may dispose, in the peripheral area 650, the particles corresponding to the environmental information about a space other than the space.

FIG. 6 illustrates a state in which first particles 601a corresponding to temperature information of a first space (e.g., an indoor space) where the electronic device is located, second particles 603a corresponding to humidity information of the first space, third particles 605a corresponding to carbon dioxide concentration information of the first space, fourth particles 607a corresponding to organic chemical concentration information of the first space, and fifth particles 609a corresponding to fine dust concentration information of the first space are disposed in the central area 630 of the screen 600, and sixth particles 601b corresponding to temperature information of a second space (e.g., an outdoor space) different from the first space, seventh particles 603b corresponding to humidity information of the second space, eighth particles 605b corresponding to carbon dioxide concentration information of the second space, ninth particles 607b corresponding to organic chemical concentration information of the second space, and tenth particles 609b corresponding to fine dust concentration information of the second space are disposed in the peripheral area 650 of the screen 600. According to an embodiment, the environmental information of the first space may be obtained based on the sensor, and the environmental information of the second space may be obtained from the external electronic device.

According to an embodiment, the electronic device (e.g., the processor 130) may set display states of the particles corresponding to the environmental information, based on data values of the environmental information. For example, with an increase in temperature, humidity, carbon dioxide concentration, organic chemical concentration, and fine dust concentration in the first space, the electronic device may increase the number, moving speed, size, or border thickness of the first to fifth particles 601a, 603a, 605a, 607a, and 609a corresponding thereto, or may make the color or the border color thereof dark. Also, with an increase in temperature, humidity, carbon dioxide concentration, organic chemical concentration, and fine dust concentration in the second space, the electronic device may increase the number, moving speed, size, or border thickness of the sixth to tenth particles 601b, 603b, 605b, 607b, and 609b corresponding thereto, or may make the color or the border color thereof dark. In contrast, with a decrease in temperature, humidity, carbon dioxide concentration, organic chemical concentration, and fine dust concentration in the first space, the electronic device may decrease the number, moving speed, size, or border thickness of the first to fifth particles 601a, 603a, 605a, 607a, and 609a corresponding thereto, or may make the color or the border color thereof light. Also, with a decrease in temperature, humidity, carbon dioxide concentration, organic chemical concentration, and fine dust concentration in the second space, the electronic device may decrease the number, moving speed, size, or border thickness of the sixth to tenth particles 601b, 603b, 605b, 607b, and 609b corresponding thereto, or may make the color or the border color thereof light.

According to an embodiment, even though the types of environmental information are the same as each other, graphical elements of particles corresponding to the environmental information may be differently set according to spaces. For example, the first particles 601a corresponding to temperature information of the first space may differ from the sixth particles 601b corresponding to temperature information of the second space in terms of the shape, color, size, border thickness, or border color thereof.

Figure 7:
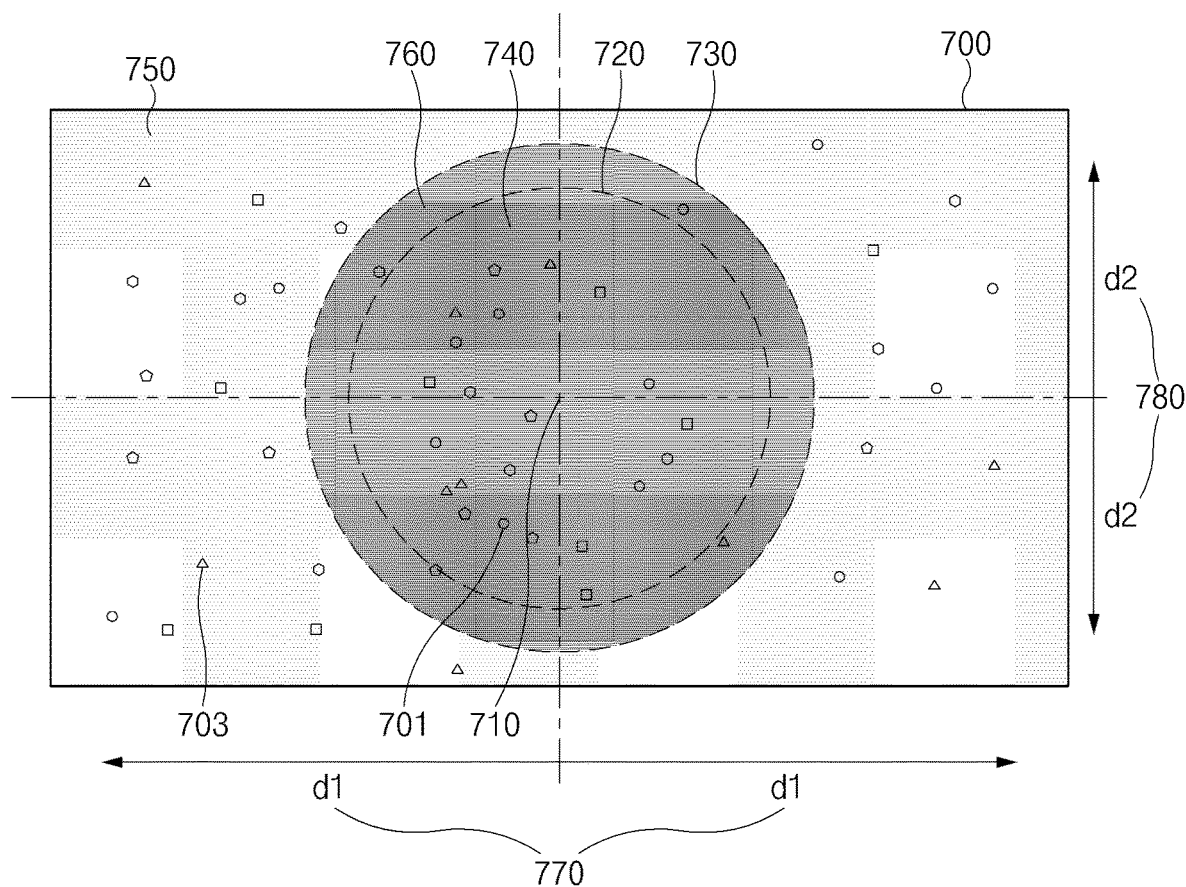
FIG. 7 is a view for explaining a change of states of dynamic particles according to an embodiment.

FIG. 7 is a view for explaining a change of states of dynamic particles according to an embodiment.

Referring to FIG. 7, an electronic device (e.g., the electronic device 100) may obtain, based on a sensor (e.g., the sensor 110), environmental information of a first space (e.g., an indoor space) where the electronic device is located, and may obtain environmental information of a second space (e.g., an outdoor space), which is different from the first space, from an external electronic device (e.g., a server in a weather center) connected thereto through a communication circuit. Furthermore, the electronic device may output, on a display (e.g., the display 150), a screen 700 including particles corresponding to the obtained environmental information. In this case, the electronic device may configure the screen 700 such that particles corresponding to the environmental information of the first space are distinguished from particles corresponding to the environmental information of the second space. For example, the electronic device may generate a boundary line (e.g., a first boundary line 720 or a second boundary line 730) that divides a central area 740 of the screen 700 from a peripheral area 750 thereof, and may dispose first particles 701 corresponding to the environmental information of the first space in the central area 740 inside the boundary line and second particles 703 corresponding to the environmental information of the second space in the peripheral area 750 outside the boundary line.

According to an embodiment, the electronic device (e.g., the processor 130) may adjust moving positions of the first particles 701 to prevent the first particles 701 from deviating from the central area 740 (or intruding into the peripheral area 750) even though the first particles 701 move, and may adjust moving positions of the second particles 703 to prevent the second particles 703 from deviating from the peripheral area 750 (or intruding into the central area 740) even though the second particles 703 move. For example, the electronic device may adjust moving positions of the first particles 701 to allow the first particles 701 to move toward a center point 710 of the screen 700 or along the boundary line when the first particles 701 move away from the center point 710 to coincide with the boundary line. In another example, the electronic device may adjust moving positions of the second particles 703 to allow the second particles 703 to move away from the center point 710 of the screen 700 or along the boundary line when the second particles 703 move toward the center point 710 to coincide with the boundary line.

According to an embodiment, the electronic device (e.g., the processor 130) may configure a buffer area 760 between the central area 740 and the peripheral area 750 of the screen 700. For example, the electronic device may generate the first boundary line 720 at a position spaced apart from the center point 710 of the screen 700 by a first distance (or a first radius) and may generate the second boundary line 730 at a position spaced apart from the center point 710 of the screen 700 by a second distance (or a second radius) greater than the first distance. Accordingly, the central area 740 may be allocated inside the first boundary line 720, the buffer area 760 may be allocated between the first boundary line 720 and the second boundary line 730, and the peripheral area 750 may be allocated outside the second boundary line 730.

According to an embodiment, the electronic device (e.g., the processor 130) may set moving positions of the first particles 701 to allow the first particles 701 disposed in the central area 740 to move to the buffer area 760 beyond the central area 740. Furthermore, the electronic device may set moving positions of the second particles 703 to allow the second particles 703 disposed in the peripheral area 750 to move to the buffer area 760 beyond the peripheral area 750. According to an embodiment, the electronic device may adjust moving positions of the first particles 701 to prevent the first particles 701 from intruding into the peripheral area 750 even though the first particles 701 move to the buffer area 760, and may adjust moving positions of the second particles 703 to prevent the second particles 703 from intruding into the central area 740 even though the second particles 703 move to the buffer area 760.

According to an embodiment, the electronic device (e.g., the processor 130) may differently set moving speeds of the particles in the central area 740, the peripheral area 750, and the buffer area 760 of the screen 700. For example, the electronic device may decrease moving speeds of particles having entered the buffer area 760. For example, when the first particles 701 move at a first speed in the central area 740 and then enter the buffer area 760, the electronic device may move the first particles 701 at a second speed lower than the first speed, and when the second particles 703 move at a third speed in the peripheral area 750 and then enter the buffer area 760, the electronic device may move the second particles 703 at a fourth speed lower than the third speed. Furthermore, when the first particles 701 move at the second speed in the buffer area 760 and then return to the central area 740, the electronic device may move the first particles 701 at the first speed, and when the second particles 703 move at the fourth speed in the buffer area 760 and then return to the peripheral area 750, the electronic device may move the second particles 703 at the third speed.

According to an embodiment, the electronic device (e.g., the processor 130) may differently set moving speeds of the particles according to a separation distance (e.g., a horizontal distance d1 770 or a vertical distance d2 780) from the center point 710 of the screen 700. For example, the electronic device may decrease moving speeds of the particles with an increase in the horizontal distance 770 or the vertical distance 780. Alternatively, the electronic device may compute a separation distance from the center point 710 by using the horizontal distance 770 and the vertical distance 780 and may decrease moving speeds of the particles with an increase in the separation distance from the center point 710.

Figure 8:
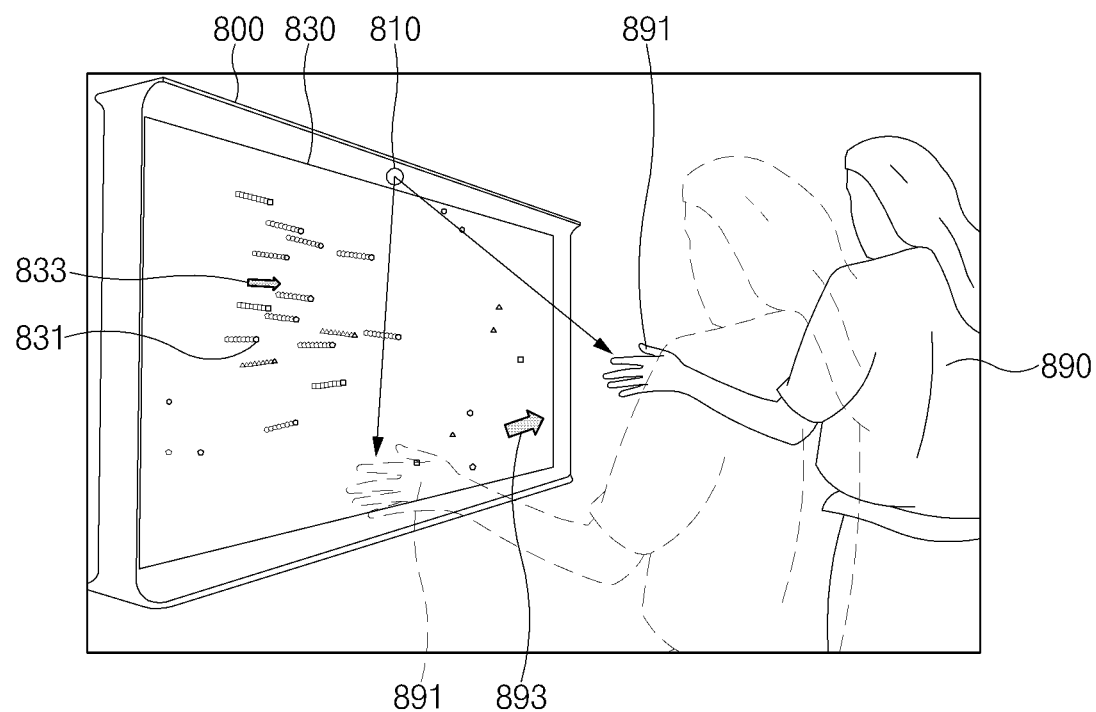
FIG. 8 is a view for explaining screen control based on a user's motion according to an embodiment.

FIG. 8 is a view for explaining screen control based on a user's motion according to an embodiment.

Referring to FIG. 8, an electronic device 800 (e.g., the electronic device 100) may take an image of a user 890 with a camera 810 and may analyze the image to determine a motion of the user 890. For example, the electronic device 800 may determine a moving direction and a moving speed of the user 890 by tracking a feature point corresponding to the user 890, among feature points included in the image.

According to an embodiment, the electronic device 800 may set a moving direction and a moving speed of particles 831 output on a display 830, based on the motion of the user 890. For example, the electronic device 800 may change positions of the particles 831 to correspond to a change in the position of the user 890. According to various embodiments, the electronic device 800 may determine a motion of a body part 891 (e.g., a hand) of the user 890 and may set a moving direction and a moving speed of the particles 831, based on the motion of the body part 891 of the user 890. As illustrated in FIG. 8, when the body part 891 of the user 890 moves in the state in which the body part 891 is in proximity to a screen of the display 830, the electronic device 800 may move the particles 831, which are disposed in a screen area close to the body part 891, based on a moving direction 893 and a moving speed of the body part 891. For example, when the body part 891 of the user 890 moves at a first speed in the first direction, e.g. the moving direction 893, the electronic device 800 may move the particles 831 at a second speed identical or similar to the first speed in a second direction 833 identical or similar to the first direction, e.g. the moving direction 893.

According to an embodiment, in the case where the particles 831 are configured to move in only areas divided from each other by a boundary line as illustrated in FIG. 6 or 7, the electronic device 800 may adjust moving positions of the particles 831 such that the particles 831 move in only specified areas according to the motion of the user 890 (or the motion of the body part 891 of the user 890). For example, the electronic device 800 may adjust moving positions of the particles 831 to prevent the particles 831 disposed in each area (e.g., a central area or a peripheral area) from passing through the boundary line even though the motion of the user 890 (or the motion of the body part 891 of the user 890) passes over the boundary line (e.g., the boundary line 610, the first boundary line 720, or the second boundary line 730) on the screen.

Figure 9:
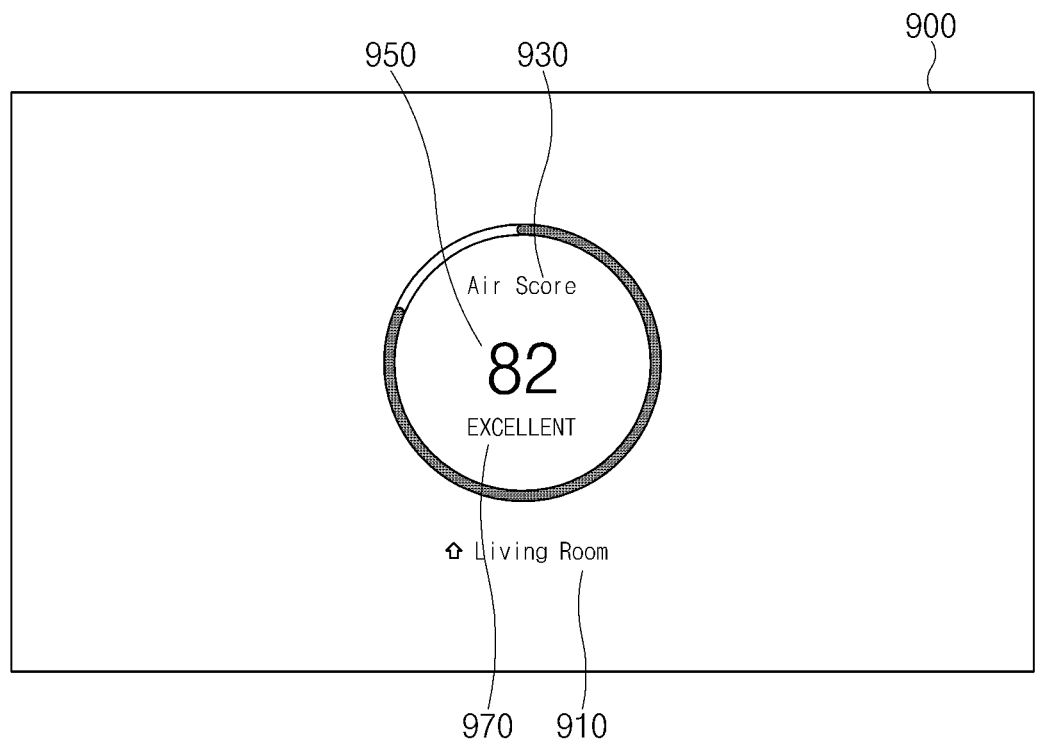
FIG. 9 is a view for explaining a screen for providing information according to an embodiment.

FIG. 9 is a view for explaining a screen for providing information according to an embodiment.

Referring to FIG. 9, an electronic device (e.g., the electronic device 100) may obtain a user's interaction through an input device (e.g., a microphone, a touch sensor, or a physical button) or a sensor (e.g., the sensor 110). For example, the electronic device (e.g., the processor 130) may obtain the user's speech through the microphone, may obtain the user's touch input through the touch sensor, or may receive a signal generated from the physical button. In another example, the electronic device (e.g., the processor 130) may determine (detect) the user's proximity to the electronic device through the sensor (e.g., a proximity sensor).

The electronic device (e.g., the processor 130) may determine whether the user's interaction satisfies a specified condition. The electronic device may determine whether the user's interaction obtained through the input device or the sensor corresponds to a user input associated with outputting detailed information about an external environment. For example, the electronic device may perform speech recognition on speech data received through the microphone and may determine whether a command to output the detailed information about the external environment is included in the speech recognition result. Alternatively, the electronic device may analyze a touch input obtained through the touch sensor and may determine, based on the analysis result, whether the touch input corresponds to a user input for selecting a display object configured to output the detailed information about the external environment. In another case, the electronic device may determine whether the physical button corresponds to a physical button configured to output the detailed information about the external environment. In another case, the electronic device may determine, through the sensor (e.g., a proximity sensor), whether the user is within a specified distance.

According to an embodiment, if the user's interaction satisfies the specified condition, the electronic device (e.g., the processor 130) may output a screen 900 including detailed information about an external environment on a display (e.g., the display 150). The screen 900 including the detailed information about the external environment may include an overall environmental index for a space where the electronic device is located. For example, as illustrated in FIG. 9, the screen 900 including the detailed information about the external environment may include position information 910 of the space, a title 930 of the information displayed on the screen 900, an environmental index 950, or environmental assessment information 970.

The position information 910 of the space may include, for example, an image and/or text representing the space where the electronic device is located. The environmental index 950 may include information that expresses environmental assessment of the space as a percentage. For example, the environmental index 950 may be numerical information determined depending on whether temperature, humidity, carbon dioxide concentration, organic chemical concentration, or fine duct concentration in the space is within a specified range, or how much temperature, humidity, carbon dioxide concentration, organic chemical concentration, or fine duct concentration in the space deviates from the specified range. The environmental assessment information 970 may include information that represents an influence of an environment for the space on the user in a stepwise manner, based on the environmental index 950. For example, the environmental assessment information 970 may be displayed as "poor" when the environmental index 950 is less than a first value, "good" when the environmental index 950 is greater than or equal to a second value, or "fair" when the environmental index 950 is greater than or equal to the first value and less than the second value. However, the environmental assessment information 970 is not limited thereto. According to various embodiments, the environmental assessment information 970 may be divided into more steps.

Figure 10:
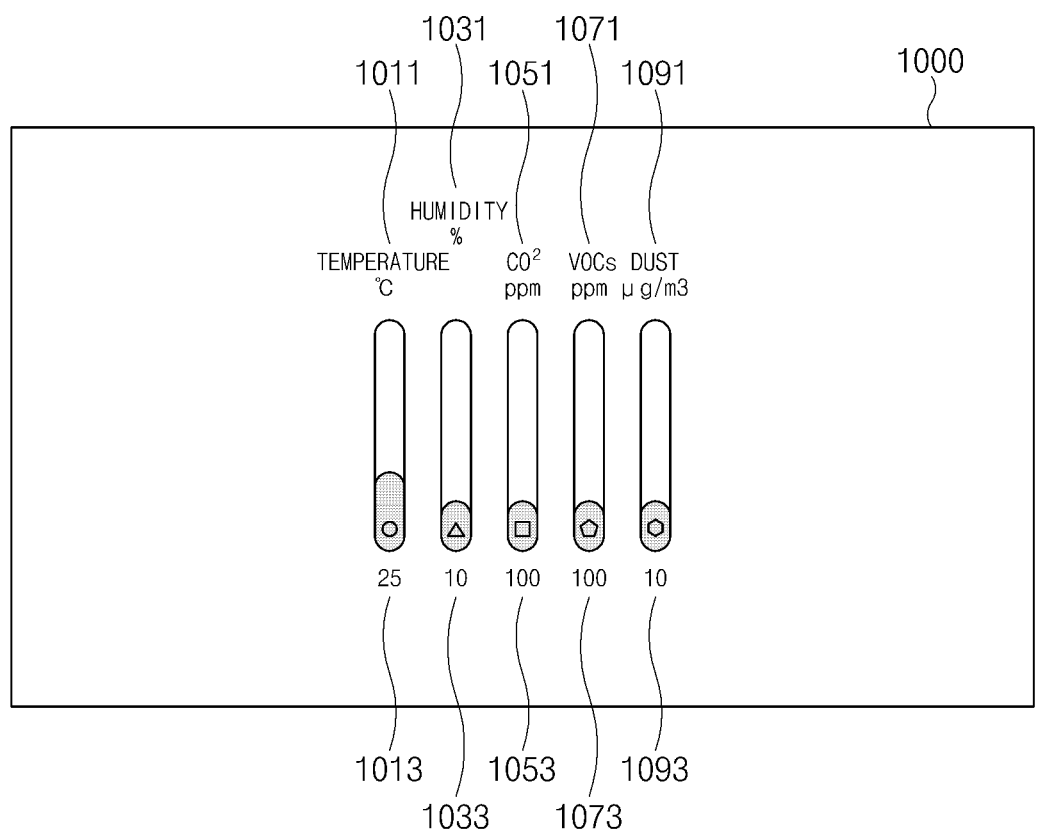
FIG. 10 is a view for explaining a screen for providing information according to another embodiment.

FIG. 10 is a view for explaining a screen for providing information according to another embodiment.

Referring to FIG. 10, an electronic device (e.g., the electronic device 100) may obtain a user's interaction through an input device (e.g., a microphone, a touch sensor, or a physical button) or a sensor (e.g., the sensor 110), and if the user's interaction satisfies a specified condition, the electronic device may output, on a display (e.g., the display 150), a screen 1000 including detailed information about an external environment.

According to an embodiment, the electronic device (e.g., the processor 130) may configure the screen 1000 by classifying the environmental information according to the types thereof. For example, the electronic device may configure the screen 1000 such that temperature information, humidity information, carbon dioxide concentration information, organic chemical concentration information, and fine dust concentration information are distinguished from one another. As illustrated in FIG. 10, the screen 1000 including the detailed information about the external environment may include a title/unit 1011 of the temperature information, a temperature value 1013, a title/unit 1031 of the humidity information, a humidity value 1033, a title/unit 1051 of the carbon dioxide concentration information, a carbon dioxide concentration value 1953, a title/unit 1071 of the organic chemical concentration information, an organic chemical concentration value 1073, a title/unit 1091 of the fine dust concentration information, and a fine dust concentration value 1093.

According to an embodiment, the title/unit 1011 of the temperature information, the title/unit 1031 of the humidity information, the title/unit 1051 of the carbon dioxide concentration information, the title/unit 1071 of the organic chemical concentration information, and the title/unit 1091 of the fine dust concentration information may be represented in a text format, and the temperature value 1013, the humidity value 1033, the carbon dioxide concentration value 1053, the organic chemical concentration value 1073, and the fine dust concentration value 1093 may be represented in a text and/or graph format.

According to an embodiment, if the user's interaction satisfies the specified condition, the electronic device may selectively output the screen 900 illustrated in FIG. 9 or the screen 1000 illustrated in FIG. 10, or may sequentially output the screen 900 and the screen 1000. For example, the electronic device may output the screen 1000 illustrated in FIG. 10 after the screen 900 illustrated in FIG. 9 is output and specified time elapses.

According to various embodiments, at least a part of an apparatus (e.g., modules or functions thereof) or a method (e.g., operations) may be, for example, implemented by instructions stored in a computer-readable storage media in the form of a program module. The instruction, when executed by a processor, may cause the processor to perform a function corresponding to the instruction. The computer-readable recording medium may include a hard disk, a floppy disk, a magnetic media (e.g., a magnetic tape), an optical media (e.g., a compact disc read only memory (CD-ROM) and a digital versatile disc (DVD), a magneto-optical media (e.g., a floptical disk)), an embedded memory, and the like. The one or more instructions may contain a code made by a compiler or a code executable by an interpreter.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. An electronic device comprising:
a sensor;
a display;
a memory storing an image reproduction application; and
a processor electrically connected with the sensor, the display, and the memory,
wherein the memory stores instructions that, when executed, cause the processor to:
control the display to display a first screen, the displayed first screen including one or more particles moving via the image reproduction application without a user input;
obtain, from the sensor, first information about an external environment that is external to the electronic device; and
control the display to display a second screen including a first particle, whose state is changed, of the one or more particles based on the first information,
wherein the memory further stores instructions that, when executed, cause the processor to:
control the display to display the first particle moved in only a first area of the first screen; and
control the display to display a second particle of the one or more particles, moved in only a second area that is located outside the first area and that surrounds the first area,
wherein the second particle is based on second information corresponding to another external environment.

2. The electronic device of claim 1, wherein the memory further stores instructions that, when executed, cause the processor to change at least one from among a shape, a size, a color, and display time of the first particle based on at least one of attributes of the first information.

3. The electronic device of claim 2, wherein the memory further stores instructions that, when executed, cause the processor to change at least one from among a position of the first particle, a number of first particles, and a moving speed of the first particle, based on at least one value measured for at least one of attributes of the first information.

4. The electronic device of claim 1, further comprising:
a camera,
wherein the memory further stores instructions that, when executed, cause the processor to:
obtain an image of a user through the camera;
determine a motion of the user, based on a result obtained by analyzing the image; and
set a moving direction and a moving speed of the first particle, based on a direction and a speed of the motion.

5. The electronic device of claim 1, further comprising:
an interface for obtaining a user's interaction,
wherein the memory further stores instructions that, when executed, cause the processor to:
obtain the user's interaction through the interface; and
control the display to output a third screen, the third screen including detailed information about the first information, when the user's interaction satisfies a specified condition.

6. The electronic device of claim 5, wherein the interface comprises at least one from among:
a proximity sensor configured to sense proximity of a user to the electronic device, a microphone configured to receive speech of the user,
a touch sensor configured to obtain a touch input of the user, and
a physical button configured to generate a signal in response to a button input of the user.

7. The electronic device of claim 1, further comprising:
a communication circuit for communication with an external electronic device,
wherein the external environment is one external environment and the memory further stores instructions that, when executed, cause the processor to:
obtain the second information about the another external environment that is external to the electronic device, from the external electronic device through the communication circuit; and
control the display to display a fourth screen including the second particle, whose state is changed, of the one or more particles based on the second information.

8. The electronic device of claim 1, wherein the memory further stores instructions that, when executed, cause the processor to differently set at least one from among a shape, a size, a color, and display time of the second particle based on an at least one of attributes of the second information.

9. The electronic device of claim 8, wherein the state of the third second particle changed based on the second information comprises at least one of a position of the second particle, a number of second particles, or a moving speed of the second particle.

10. A screen control method of an electronic device, the method comprising:
displaying a first screen including one or more particles on a display, wherein the one or more particles moving via an image reproduction application without a user input;
obtaining, from a sensor, first information about an external environment that is external to the electronic device;
obtaining, from an external electronic device, second information corresponding to another external environment that is external to the electronic device;
displaying a second screen including a first particle, whose state is changed, of the one or more particles based on the first information,
displaying the first particle moved in only a first area of the first screen; and
displaying a second particle of the one or more particles, moved in only a second area that is located outside the first area and that surrounds the first area,
wherein the second particle is based on the second information.

11. The method of claim 10, further comprising:
differently setting at least one from among a shape, a size, a color, and display time of the first particle according to at least one attribute of the first information.

12. The method of claim 11, further comprising:
differently setting at least one from among a position of the first particle, a number of first particles, and a moving speed of the first particle, based on a value measured for at least another attribute of the first information.

13. The method of claim 10, further comprising:
obtaining an image of a user through a camera;
determining a motion of the user, based on a result obtained by analyzing the image; and
setting a moving direction and a moving speed of the first particle, based on a direction and a speed of the motion.

14. The method of claim 10, further comprising:
obtaining a user's interaction of a user through an interface; and
displaying a third screen, the third screen including detailed information about the first information through the display when the user's interaction satisfies a specified condition.

* * * * *